United States Patent
Gartside et al.

(10) Patent No.: US 7,301,062 B2
(45) Date of Patent: Nov. 27, 2007

(54) PROCESS FOR THE SELECTIVE HYDROGENATION OF ALKYNES AND/OR DIENES IN AN OLEFIN-CONTAINING HYDROCARBON STREAM

(75) Inventors: Robert J. Gartside, Summit, NJ (US); Thomas Skourlis, Basking Ridge, NJ (US)

(73) Assignee: ABB Lummus Global Inc., Bloomfield, NJ (US)

( * ) Notice: Subject to any disclaimer, the term of this patent is extended or adjusted under 35 U.S.C. 154(b) by 650 days.

(21) Appl. No.: 10/899,644

(22) Filed: Jul. 27, 2004

(65) Prior Publication Data
US 2006/0025641 A1  Feb. 2, 2006

(51) Int. Cl.
C07C 5/08  (2006.01)
C07C 5/09  (2006.01)

(52) U.S. Cl. .................. 585/260; 585/259; 585/273; 585/262

(58) Field of Classification Search ............... None
See application file for complete search history.

(56) References Cited

U.S. PATENT DOCUMENTS

| | | |
|---|---|---|
| 4,126,645 A | 11/1978 | Collins |
| 4,329,530 A | 5/1982 | Irvine et al. |
| 4,404,124 A | 9/1983 | Johnson et al. |
| 4,484,015 A | 11/1984 | Johnson et al. |
| 4,533,779 A | 8/1985 | Boitiaux et al. |
| 4,551,443 A | 11/1985 | Hudson |
| 4,906,602 A | 3/1990 | Schneider et al. |
| 5,364,998 A | 11/1994 | Sarrazin et al. |
| 5,679,241 A | 10/1997 | Stanley et al. |
| 5,877,363 A | 3/1999 | Gildert et al. |
| 6,084,140 A | 7/2000 | Kitamura et al. |
| 6,169,218 B1 | 1/2001 | Hearn et al. |
| 6,420,619 B1 | 7/2002 | Gartside et al. |
| 6,486,369 B1 | 11/2002 | Voight et al. |
| 6,509,292 B1 | 1/2003 | Blankenship et al. |
| 6,734,328 B1 | 5/2004 | Ryu |

(Continued)

FOREIGN PATENT DOCUMENTS

GB        1596959        5/1978

OTHER PUBLICATIONS

Notification of Transmittal of International Search Report and Written Opinion, PCT/ISA/220 dated Dec. 8, 2005 for Appln. No. PCT/US2005/024628.

*Primary Examiner*—Tam M. Nguyen
(74) *Attorney, Agent, or Firm*—Dilworth & Barrese, LLP

(57) ABSTRACT

A process for the selective hydrogenation of one or more alkyne and/or one or more diene in an olefin-containing hydrocarbon feed includes contacting the hydrocarbon feed with a catalyst under selective hydrogenation conditions, the catalyst including from about 0.01 to about 0.1 weight percent palladium and from about 0.005 to about 0.6 weight percent of at least one Group IB metal incorporated into an inorganic support, wherein the surface area of the support is from about 2 to about 20 $m^2/g$, the pore volume is greater than about 0.4 cc/g, at least about 90% of the pore volume is contained in pores with pore diameters larger than about 500 Å, and the pore volume of the pores with a pore diameter from about 500 to about 1,000 Å comprise from about 1% to about 2% of the total pore volume.

26 Claims, 6 Drawing Sheets

U.S. PATENT DOCUMENTS 6,759,562 B2  7/2004  Gartside et al.
2004/0019245 A1  1/2004  Gartside et al.
2006/0025302 A1*  2/2006  Blankenship et al. ....... 502/330

* cited by examiner

PROCESS FOR THE SELECTIVE HYDROGENATION OF ALKYNES AND/OR DIENES IN AN OLEFIN-CONTAINING HYDROCARBON STREAM

BACKGROUND OF THE INVENTION

The present invention relates to a process for the removal of alkynes and/or dienes from gas or liquid streams of olefin-containing hydrocarbons, e.g., those derived from steam cracking or refinery processes.

The manufacture of unsaturated hydrocarbons usually involves cracking various types of hydrocarbons and often produces a crude product containing hydrocarbon impurities that are more unsaturated than the desired product. These highly unsaturated hydrocarbon impurities are often very difficult to separate by fractionation from the desired olefin product. The most common example is ethylene manufacture, in which alkynes are common by-products. For example, the effluent from steam or thermal cracking processes for the production of ethylene typically contains, as unwanted impurities, significant amounts of acetylene and $C_3$ to $C_6$ diolefins and acetylenics. Acetylene is difficult to separate from ethylene by fractionation, and conversion by hydrogenation is usually accompanied by a substantial amount of ethylene conversion to ethane. In a similar way, hydrogenation of $C_3H_4$ (methyl acetylene or allene), propadiene and butadiene results in the production of their olefin analogs, but also significant production of $C_3$ and/or $C_4$ paraffins as a result of over reaction. It has often been difficult industrially to remove such undesirable, highly unsaturated hydrocarbons by hydrogenation so that no significant hydrogenation of desired olefin hydrocarbon takes place.

Two general types of selective hydrogenation processes for removing undesired, unsaturated hydrocarbons have come into use. One, known as "front-end" hydrogenation, involves passing the crude gas in vapor phase from the initial cracking step, after removal of steam and condensable organic material, over a hydrogenation catalyst. This gas typically contains substantial quantities of hydrogen as a result of the cracking step. "Front End" is characterized as hydrogenation before hydrogen has been removed from the balance of the hydrocarbon gas. Despite the large hydrogen content of such gas, which is very greatly in excess of the amount necessary to hydrogenate the alkynes and, therefore, sufficient to hydrogenate a substantial part of the olefin present, operation with sufficient selectivity to produce olefins of polymerization quality is well established and catalyst lives of many years are obtained. In addition, there is a "front end" application involving a catalytic distillation unit and a vapor phase reactor system where the reaction occurs both in the vapor and liquid phases.

In the other type of selective hydrogenation, known as "tail-end" hydrogenation, the crude gas is fractionated and the resulting concentrated product streams are individually reacted with removed hydrogen in a slight excess over the quantity required for hydrogenation of the highly unsaturated hydrocarbons which are present. This process can occur in either the gas or liquid phase dependent upon the pressures utilized. By controlling the amount of hydrogen, the reaction selectivity to olefins can be maximized. However, this requires a multiplicity of reaction systems since following fractionation, there are individual streams of $C_2$'s (ethylene, ethane and acetylene), $C_3$'s (propylene, propane, methyl acetylene, and propadiene), $C_4$'s (butenes, butadiene, Ethyl acetylene, vinyl acetylene, and butanes), each requiring a reactor system. This results in increased capital and operating costs.

BRIEF SUMMARY OF THE INVENTION

A process is provided herein for the selective hydrogenation of alkyne and/or diene present in an olefin-containing hydrocarbon feed. The process comprises contacting the hydrocarbon feed containing at least about 10,000 ppm by weight alkyne content and/or diene with a catalyst in a first reaction zone under selective hydrogenation conditions, said catalyst including palladium and at least one Group IB metal incorporated into an inorganic support, wherein the surface area of the support is from about 2 to about 20 $m^2/g$ and a pore volume greater than about 0.4 cc/g, wherein at least about 90% of the pore volume is contained in pores with pore diameters larger than about 500 Å, and wherein the pore volume of the pores with a pore diameter from about 500 to about 1,000 Å comprise from about 1 to about 2% of the total pore volume.

The process advantageously provides greater selectivity for the hydrogenation of alkynes and higher olefins.

BRIEF DESCRIPTION OF THE DRAWINGS

Various embodiments are described below with reference to the drawings wherein.

DETAILED DESCRIPTION OF THE INVENTION

Figure 1:
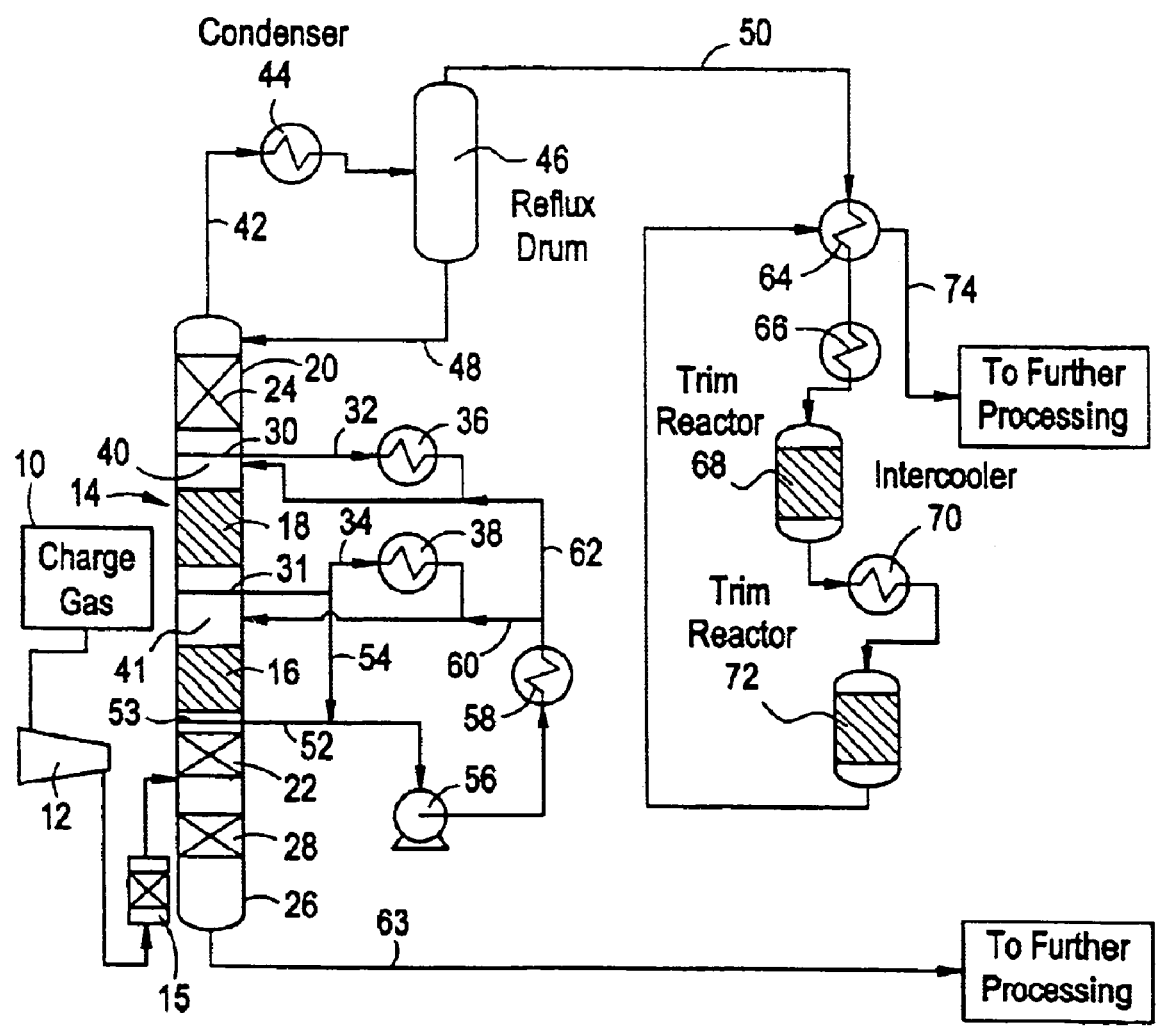
FIG. 1 is a flow diagram illustrating the present invention.

This invention relates to selective hydrogenation of alkynes and/or dienes present in an olefin-containing hydrocarbon raw gas feed such as the effluent from a cracking unit or to the selective hydrogenation of alkynes and/or dienes in an olefin-containing hydrocarbon stream that has undergone minimal fractionation to remove certain heavy components but still contains substantial amounts of hydrogen and highly unsaturated components.

A particular purpose of the process is to selectively hydrogenate $C_2$ to $C_6$ alkynes and/or dienes to their olefin analogs starting with a cracked gas effluent mixture containing, e.g., acetylene and a significant amount of higher ($C_3$ to $C_6$) diolefins and possibly other acetylenics in the presence of one or more olefins, hydrogen and trace quantities of other impurities. In particular, raw gas feed typically contains, in addition to acetylene, over 10,000 ppm of methyl acetylene, propadiene, 1,3-butadiene, ethyl acetylene, vinyl acetylene, isoprene and other $C_5$ dienes. These impurities are often hard to hydrogenate out of the feed and can only be completely hydrogenated after a substantial amount of ethylene is hydrogenated to ethane. The process of the present invention is based on an improved high pore volume and unique pore volume distribution catalyst developed by Sud-Chemie, Louisville, Ky. (hereinafter, "Sud Chemie catalyst" or "improved catalyst"). The preferred Sud Chemie catalyst for use in the process described below is based on a low surface area inorganic oxide support impregnated by Pd and modified by Ag or other Group IB metal compound.

More particularly, the preferred Sud Chemie catalyst for use in the process of the invention includes a low surface area catalyst carrier, such as alumina, silica-alumina, zinc oxide, nickel spinel, titania, zirconia, ceria, chromia-alumina, magnesium oxide, cerium oxide and mixtures thereof. The preferred carrier is an alumina carrier. To qualify as a "low surface area" carrier, the carrier has a surface area less than about 20 $m^2/g$, preferably from about 2 to about 20 $m^2/g$, more preferably from about 2 to about 10 $m^2/g$, and most preferably from about 3 to about 5 $m^2/g$ as measured using the nitrogen method of determining surface area. The pore volume of the carrier is greater than about 0.4 cc/g, preferably greater than about 0.45 cc/g, and most preferably greater than about 0.5 cc/g. In addition, the carrier is selected such that at least about 90%, preferably at least about 95%, and most preferably at least about 98% of the pore volume, is contained in pores with pore diameters greater than about 500 Å, and wherein the pore volume of pores with pore diameters from about 500 to about 1,000 Å is from about 1 to about 2% of the total pore volume. It is important that carrier materials be selected containing this particular pore volume and pore volume distribution to provide catalysts with enhanced performance, particularly enhanced selectivity and minimal loss of desired hydrocarbons, especially for selective hydrogenation reactions.

The catalyst carrier can be formed in any suitable shape, such as a sphere, cylinder, trilob, tablet and the like. In one preferred embodiment, the catalyst carrier is a sphere. The catalyst carrier can also be formed in any suitable size, preferably a sphere with a diameter from about 1 to about 5 mm, and more preferably from about 1 to about 3 mm.

The palladium can be introduced into the catalyst carrier by any conventional procedure which produces the desired palladium loading. One preferred technique involves impregnating the catalyst carrier with an aqueous solution of a palladium compound such as palladium chloride. Preferably, the depth of penetration of the palladium compound into the carrier is controlled so that at least about 90 percent of the palladium compound is contained within about 250 microns of the surface of the catalyst carrier. Any suitable method can be used to control the depth of palladium penetration such as that disclosed in U.S. Pat. Nos. 4,484,015 and 4,404,124, the contents of which are incorporated herein by reference.

After palladium impregnation, the impregnated material is calcined at a temperature from about 100° C. to about 600° C., preferably for at least about three hours. The palladium compound contained in the palladium catalyst precursor is then reduced, preferably by wet reducing, using a suitable wet reducing medium such as sodium formate, formic acid, hydrazine, alkali metal borohydrides, formaldehyde, ascorbic acid, dextrose or other known or conventional wet reducing agent.

Once the precursor catalyst material has been reduced, it is washed with deionized water to remove any halides, such as chlorides, to a level of less than about 100 ppm. The reduced catalyst composition is then dried at about 100° C. to about 600° C.

The palladium impregnated precursor catalyst is then further impregnated with one or more Group IB metal compounds such as Ag, Cu and Au, as an additive or additives. These compounds are preferably selected from silver salts, gold salts and/or copper salts or mixtures thereof. Preferably, the metal additive is silver impregnated in the form of a silver salt. The Group IB additive can be impregnated in the palladium impregnated precursor catalyst by any conventional process such as by soaking or spraying the palladium impregnated precursor catalyst with an aqueous solution of the Group IB metal compound. For example, if the Group IB metal is silver, in one preferred embodiment the aqueous solution can be a silver nitrate solution. After impregnation, the palladium impregnated catalyst material with the Group IB metal additive is then calcined at a temperature from about 100 to about 600° C. for at least about three hours. The catalyst is then reduced, preferably by heat treating with hydrogen, e.g., for about 1 hour at about 80 to about 120° C.

The amount of palladium present on the catalyst can range from about 0.01 to about 0.1 weight percent, preferably from about 0.01 to about 0.05 weight percent and most preferably from about 0.01 to about 0.03 weight percent, based on the total weight of the catalyst. The amount of the Group IB metal additive, preferably silver, that may be added can range from about 0.005 to about 0.6 weight percent, preferably from about 0.01 to about 0.3 weight percent, and most preferably from about 0.01 to about 0.12 weight percent based on the total weight of the catalyst. The ratio of the Group IB additive present on the catalyst to the palladium is from about 0.5:1 to about 6:1, preferably about 1:1 to about 6:1 and most preferably from about 1:1 to about 4:1.

Following final drying, the palladium catalyst with Group IB metal additive is ready for use in a selective hydrogenation reactor, for example, one suitable for the selective hydrogenation of impurities such as butadiene, alkynes (acetylenics) and diolefins, particularly in a raw gas feed stream, without separation of individual components.

The palladium catalyst with the Group IB additive employed in the process of the invention is designed primarily for the selective hydrogenation of impurities, such as acetylenics and diolefins, in admixture with other hydrocarbons, $H_2$ and CO, particularly in a raw gas feed stream. When the process is front end selective hydrogenation of a raw gas feed stream, the feed stream without separation normally includes substantial quantities of hydrogen, methane, $C_2$, $C_3$, $C_4$, $C_5$ and trace quantities of higher hydrocarbons, small quantities of carbon monoxide and carbon dioxide, as well as various impurities, such as 1,3-butadiene, acetylenics and diolefins, and may be wet or dry. The goal of the selective hydrogenation reaction is to reduce substantially the amount of the impurities present in the feed stream without substantially reducing the amount of desired hydrocarbons that are present.

In use, the palladium catalyst with Group IB metal additive is placed in a reactor. The inlet temperature of the feed stream in the reactor is raised to a level sufficient to hydrogenate the acetylene. Any suitable reaction pressure can be used. Generally, the total pressure is in the range of about 600 to about 6,750 kPa with the gas hourly space velocity (GHSV) in the range of about 1,000 to about 14,000 liters per liter of catalyst per hour.

The catalyst of the invention can be used for gas phase, liquid phase or combination gas and liquid phase applications. Regeneration of the catalyst may be accomplished by heating the catalyst in air at a temperature, preferably not in excess of 500° C., to burn off any organic material, polymers or char.

The subject catalyst exhibits improved hydrogenation of impurities, such as methylacetylene, butadiene, and isoprene, in comparison to prior art catalysts. The presence of these higher acetylenics and diolefins improves the recovery of ethylene. The improved performance characteristics is not obvious from performance testing in the absence of impurities such as methylacetylene (MA), propadiene (PD), butadiene (BD), isoprene, and the like.

The process of the invention can advantageously be used for the following applications:

1. Front End Catalytic Distillation with Trim Reactor.

The catalyst described herein can advantageously be used in a selective hydrogenation process and system as described in U.S. patent application Publication US 2004/0019245A1 (U.S. patent application Ser. No. 10/202,702 filed Jul. 24, 2002) entitled "Olefin Plant Recovery System Employing a Combination of Catalytic Distillation and Fixed Bed Catalytic Steps", which is herein incorporated by reference in its entirety. The fixed bed trim reactor is essential to achieve 100% acetylene hydrogenation of the catalytic distillation overhead. The overall objective of front-end catalytic distillation-hydrogenation unit is the conversion of acetylene, methyl acetylene, propadiene, butadiene, and $C_5$ diolefins to corresponding mono-olefins while minimizing all propylene and ethylene losses. The hydrogenation occurs primarily in the liquid phase within the catalytic distillation unit although some small amount occurs in the vapor phase. In order to achieve an ethylene gain, small amounts of acetylene as well as other dienes and acetylenics remain unconverted from the catalytic distillation unit. The catalytic distillation unit typically operates at a temperature of 85 to 130 C. and at pressures from 5 to 15 $kg/cm^2$.

A trim reactor operating in the gas phase is placed downstream from the catalytic distillation unit in order to treat the overhead product and achieve the acetylene specification required for polymer grade ethylene (which is 0 ppm). The operation of the combined catalytic distillation unit and trim reactor will typically be accompanied by carbon monoxide (CO) disturbances, variations in diene and acetylenic feed concentrations, catalyst deactivation, as well as other foreseeable processing upsets resulting from both variations in the cracking operation as well as from process upsets. In particular, CO concentration swings can lead to thermal excursions in front end reactors. Changes in CO feed concentration from the design mole percent of about 0.05% up to a maximum of about 0.2%, as expected on a weekly cycle for a typical ethylene cracker, will lower the activity of any catalyst and thus will lower the hydrogenation of the alkynes and dienes. Maintaining stable conversion of the alkynes and dienes without hydrogenating the olefins is extremely difficult without the presence of fixed bed reactors. A fixed bed (trim) reactor has the ability to quickly adjust the inlet temperature. This provides more efficient handling of increases or decreases in CO than having to modify the operation of the catalytic distillation. With the use of the trim reactor, significant ethylene gains of about 0.2%, representing nearly about 35% ethylene selectivity with 100% acetylene conversion and 5000 ppm or less total outlet $C_3$ and heavier dienes and acetylenics, is possible.

2. Raw Gas "Front End" Acetylene Converter.

In conventional ethylene plant technology, LPG crackers can produce raw gas feed streams from cracking facilities containing $C_2$, $C_3$, $C_4$, $C_5$, and trace quantities of $C_6$ and higher hydrocarbons as well as hydrogen and methane. These raw gas feeds can also contain significant impurities such as 1,3-butadiene, methyl acetylene, propadiene, acetylene, isoprene, and trace quantities of other hydrocarbon impurities. The present application can be used in "front end" hydrogenation systems used to remove acetylene, while at the same time the other impurities are also hydrogenated to useful olefinic components.

In a typical "front end raw gas converter", the cracked gas from the compression section and acid gas removal section is fractionated to remove heavy highly unsaturated materials (methyl acetylene, propadiene, butadiene, for example). The reaction takes place in the vapor phase over a fixed bed (or series of fixed beds) with intercooling. It is well known in the industry that if the concentration of the acetylenes and/or dienes exceed 10,000 ppm, then the adiabatic temperature rise as a result of the hydrogenation will be such that a runaway reaction will occur.

Typically, the hydrogen gas concentration is greater than the stoichiometric amount needed for complete hydrogenation of the impurities that are present in the crude gas. To minimize the risk of the excess hydrogen gas hydrogenating ethylene in the feed stream, the hydrogenation catalyst must be very selective and have a high tolerance for CO variations. If the catalyst is not selective or tolerant, then a greater amount of hydrogenation will take place, destroying olefins. Further, this greater amount of hydrogenation in the vapor phase will release additional heat raising the temperature of the reaction and thus increasing the rate of hydrogenation even further. This will ultimately result in a runaway unless controlled. It is also important to achieve this high selectivity not just at the low start of run (SOR) temperature but in as wide a temperature range as possible, since temperature variations are necessitated for controlling the conversion during CO spikes as well as by catalyst deactivation end of run (EOR) conditions. A low selectivity of acetylene to ethylene at higher temperatures can lead to reaction runaways, since both ethylene and hydrogen are in great excess. This can be especially true when CO is reduced from a spike back to a normal level or as the end of the run is approached.

Typical reaction conditions for selective hydrogenation include a temperature of from about 60° F. to about 200° F., a pressure of from about 100 psig to about 250 psig, and a space velocity of from about 1,000 to about 5,000 GHSV. Under typical processing conditions and using a conventional Pd Catalyst all the acetylene and a substantial portion of the higher dienes and acetylenics are hydrogenated only when a substantial portion of ethylene is hydrogenated to ethane.

Referring now to FIG. 1 in one embodiment of the present invention, the charge gas 10, an effluent from a cracking process, is compressed at 12 to between 150 and 250 psig and then fed to the catalytic distillation column 14. The charge gas may or may not be preheated to match column temperatures. The charge gas would typically pass through one or more guard beds 15 to remove such poisons as lead (Pb), arsenic (As) and mercury (Hg). These are known catalyst poisons and the guard beds would be employed in a known manner to protect the catalytic distillation catalyst. Entering the catalytic distillation column, the 8% to 20% by weight diene and acetylenic feed is hydrogenated in catalyst beds 16 and 18 located in the rectification section 20 of the column. The catalytic beds include the Sud Chemie catalyst as described above. The catalyst used within a catalytic distillation column consists of either a single catalyst or several catalysts of the same type with different metal loadings to adjust activity located in different portions of the column. Referring again to the selective hydrogenation process and system as described in U.S. patent application Publication US 2004/0019245A1 entitled "Olefin Plant Recovery System Employing a Combination of Catalytic Distillation and Fixed Bed Catalytic Steps", it is possible (FIG. 3) within the lower sections of the catalytic distillation tower or in the fixed bed pre-reactor (78) preceding the catalytic distillation tower, or both, to include a catalyst that is not of the Sud Chemie type described above but one that has a functionality to tolerate and remove selective poisons such as mercaptans prior to their contacting the Sud Chemie catalyst without departing from the invention since the bulk of the reaction will occur over the Sud Chemie catalyst.

The hydrogenation occurs in the liquid phase in catalytic distillation fashion. Although only two reactive catalytic beds 16 and 18 are shown, this is only by way of example and could be any number of beds depending on the requirements of any particular plant or the desire to adjust catalyst activity through the use of more complex catalyst systems. Fractionation internals 22 and 24, which may be trays or packing, are provided in the rectification section 20. Additional fractionation internals could be located between the catalyst beds 16 and 18. The stripping section 26 contains fractionation internals 28.

The overhead 42 from the column is cooled in the overhead condenser 44 with cooling water or with refrigeration as needed and the resulting vapor and liquid are separated in the reflux drum 46. The resulting liquid from reflux drum 46 is fed through line 48 back into the column as reflux. The overhead vapor 50 contains most of the $C_5$ and lighter compounds while the liquid phase 48 is used to reflux the column. The vapor overhead 50 however does not pass into subsequent fractionation but into a vapor phase fixed bed reactor system consisting of one or more beds of catalyst with provision for heating and/or cooling the vapor feed. Overhead 50 is first exchanged against final fixed bed reactor system effluent 74 to recover heat. It then passes to heater 66 where the temperature of the vapor entering the first fixed bed reactor 68 (containing the Sud Chemie catalyst) is controlled. In reactor 68, some portion of the $C_2$ acetylene as well as some portion of the $C_3$ and heavier alkynes and dienes that were not converted in the catalytic distillation column are hydrogenated. The conditions and the number of fixed bed reactors employed are such that the $C_2$ acetylene is completely removed from effluent stream 74 with no loss of ethylene and propylene over the entire system (catalytic distillation plus fixed bed reactors). The addition of the fixed bed reactor system to the catalytic distillation column dramatically increases both the performance of the entire system and the ability of that system to respond to process variations and catalyst deactivation.

The operating criteria for the rectification section of the catalytic distillation column is that conditions be created wherein the unsaturated hydrocarbons are hydrogenated to the extent possible without any hydrogenation of ethylene and propylene. This is accomplished by:

1. Operating the column such that ethylene and propylene in the liquid phase is minimized, and
2. Operating the catalytic distillation column such that there are still unconverted $C_2$ to $C_5$ alkynes and diolefins remaining in column overhead 50.
3. Utilizing the Sud Chemie Catalyst to Achieve High Selectivity In the catalytic distillation operation of the present invention, the distillation function is designed and operated to distill essentially all of the $C_5$ and lighter components as overhead and essentially all of the $C_6$ and heavier components as bottoms. Alternately, the split could be at the $C_4$ carbon number where essentially all of the $C_4$ and lighter components go overhead and the $C_5$ and heavier components leave as bottoms. In order to selectively hydrogenate the acetylene, the $C_3$ alkynes and dienes, and the $C_4$ and heavier alkynes, dienes and olefins while leaving the ethylene and propylene unhydrogenated, the rectification section 20 is operated such that there is a substantial concentration gradient of $C_4$ and $C_5$ materials relative to $C_2$ and $C_3$ materials in the liquid phase where the majority of the hydrogenation reaction occurs. This can be controlled by variation of reboiler duty and reflux rate to achieve the desired overhead and bottoms composition.

The choice of operation of the catalytic distillation column as either a depentanizer or a debutanizer will be a function of both the composition of the feed and the desired hydrogenation requirements for the products. The preferred operating conditions for a depentanizer will be a pressure of from about 75 psig to about 350 psig and a catalyst bed temperature of from about 50° C. to about 150° C. Similarly, the preferred operating conditions for a debutanizer column will be a pressure of from about 100 psig to about 400 psig and a catalyst bed temperature of from about 30° C. to about 130° C.

Figure 2:
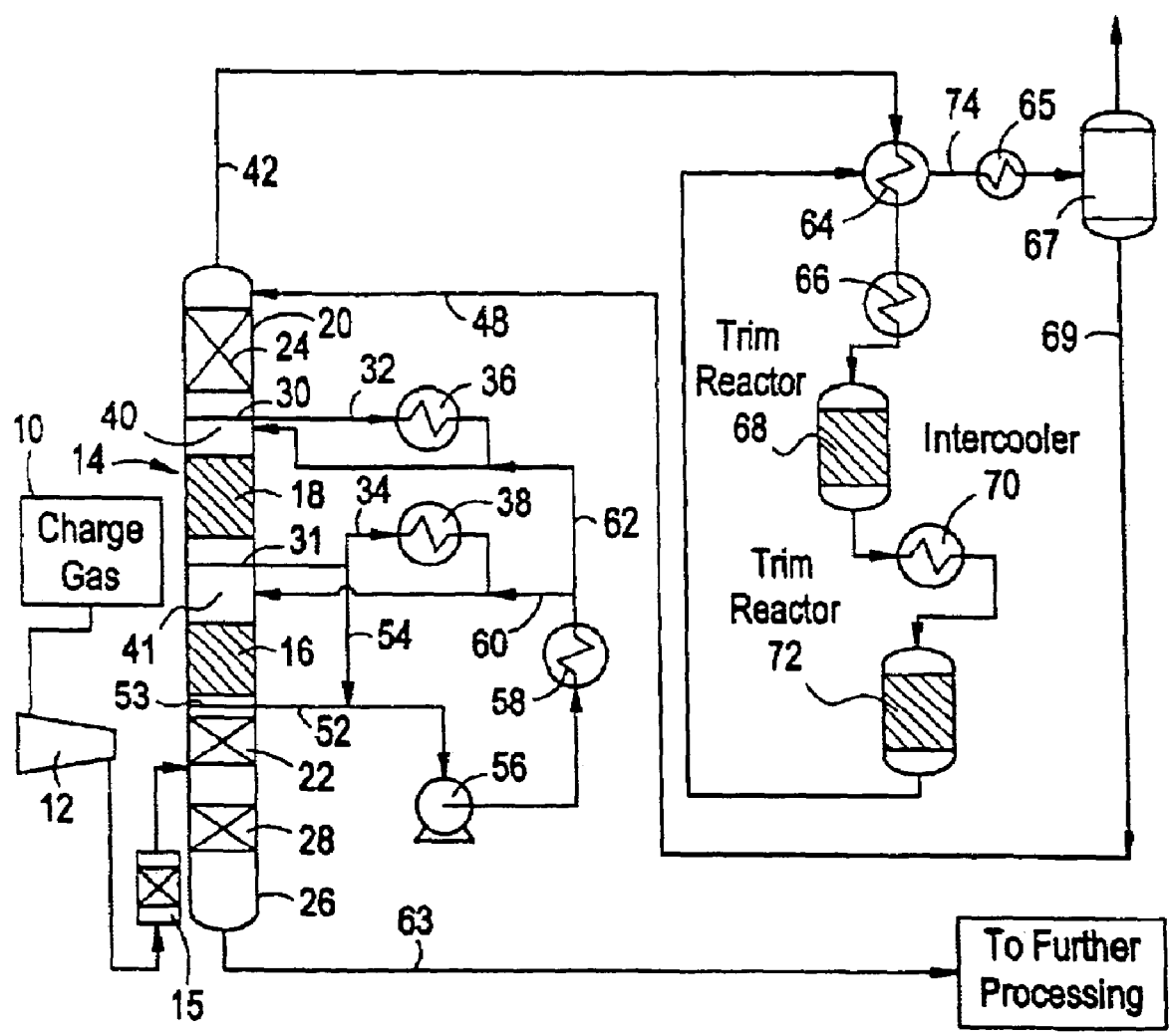
FIG. 2 is a flow diagram similar to FIG. 1 but illustrating another embodiment of the present invention.

In addition to controlling the overall fractionation, the temperature and composition profiles over the reactive sections can be controlled by adjusting the rates of heat removal over the column and by recirculation of liquid within and/or around the catalyst beds. As shown in FIG. 2, trays 30 and 31 collect the descending liquid which is withdrawn as side streams 32 and 34. These streams may or may not pass through the intercoolers 36 and 38 and then be reinjected back into the column through the distribution headers 40. This permits a portion of the heat of reaction to be removed in the intercoolers. By arranging the intercoolers in this fashion, the cooling medium can be water while the cooling in the overhead condensers may need to be at least partly provided by mechanical refrigeration. Hence, the use of the intercoolers can significantly reduce the portion of the heat of reaction which needs to be removed by mechanical refrigeration.

The hydrogenation in the column 14 occurs in the liquid phase over the Sud Chemie catalyst. The extent of the reaction is dependent upon the relative reactivity of the various components and the concentration of these components in the liquid phase at any particular point in the column. The $C_2$ and $C_3$ alkynes and dienes are far more reactive than ethylene and propylene so that they react first and rapidly. However, the relative reactivities of ethylene, propylene and the $C_4$ and heavier olefins, dienes and alkynes are very close. In order to react a significant quantity of the $C_4$ and heavier olefins, dienes and alkynes without any significant loss of ethylene and propylene, the concentration of the ethylene and propylene in the liquid phase must be minimized and the concentration and temperature profiles from top to bottom must be controlled. Since this stage of the hydrogenation occurs in a fractionation column, this control can be accomplished by adjusting the overhead reflux produced by the overhead condenser 44 and the side stream reflux from the intercoolers 36 and 38. The liquid compositions of ethylene and propylene can be kept low in the reactive zones through increases in the flow of reflux 48 and/or increased interbed cooling at 36 and 38.

The system described herein provides the flexibility to have both uncooled and cooled pumparounds in the catalyst zones 16 and 18 within the rectification section 20. This improvement permits the desired temperature and composition control with minimal disturbance to the overall distillation. This is accomplished by drawing off pumparound liquid immediately below the catalyst beds as stream 52 and/or 54 from withdrawal points 53 and 31 respectively and returning it through the pump 56 and heat exchanger 58 to the top of the same bed as streams 60 and/or 62. Alternatively, the liquid can be drawn from the bottom most catalyst bed and returned to the highest bed via stream 62. Cooling at 58 can be used, if necessary, to provide combined composition adjustment and intercooling between reactive beds. For example, while withdrawal intercooling stream 34 from point 31, cooling that stream in exchanger 38 and returning the flow to distribution system 41 will cool the liquid but not change the composition. However, withdrawing the same liquid from 31, passing it via line 54 through pump 56 to exchanger 58, cooling the liquid and returning it to liquid distributor 40 above the catalyst bed will change the composition profile within the column. This design flexibility can be used to maximize the efficiency of the hydrogenation. In this fashion, the option of cooling against a warmer cooling medium available in the prior art is maintained with the modified pumparound/intercooler reducing the expensive low level cooling required in the overhead system. Further, the heat removed by these pumparound streams can be utilized elsewhere in the ethylene plant to reduce energy consumption. Another advantage of the pumparound scheme is that it allows for relatively large liquid flow without affecting the overall column separation performance due to heavies in the overhead as in the prior art. With the large liquid flows, the pumparound can provide the necessary liquid loading over the catalyst without the need for additional reflux. This permits operation of the catalytic distillation column at lower reflux ratios than previously possible without the penalty in distillation efficiency observed with the prior art. Reflux ratios in the range of from about 0.5 to about 1.8 by weight are satisfactory for producing the necessary catalyst liquid wetting where values as high as about 5 were required with the prior art. In addition to the obvious reduction in energy requirements, higher hydrogen partial pressures due to the lower reflux ratios will be available in the present invention resulting in lower required catalyst volumes.

In a catalytic distillation column, it is critical to keep the catalyst wetted at all times to insure that the reaction occurs in the liquid phase. The selectivity of a catalytic distillation system relies in part on the reaction taking place in the liquid phase while certain components that the operator wishes to remain unreacted such as ethylene remain in the highest concentration in the vapor phase. Maintaining a certain liquid traffic down the column is critical to keeping the catalyst wetted. If the liquid traffic is greater than 800 lb liquid/hr/ft$^2$ of column cross-section, the catalyst will be highly wetted and reaction selectivity will be maintained.

A secondary control variable would be variation in the reflux with associated variation in reboiler duty. In this way, both catalyst bed temperature and composition may be altered to achieve the desired hydrogenation.

Additionally, a variable feed location allowing for a main feed point below the stripping section 22 will provide some separation of any heavy components present in the feed before reaching both the catalyst bed 16 and the side stream 52 for the first pumparound. In this way, circulating the heavy, potentially fouling components over the catalyst bed is eliminated. In addition, feed points above the first catalyst bed can be incorporated to allow for turndown operation and thus avoid the problems of excess catalyst and resultant selectivity loss under these lower flow conditions. The bottoms 63 from the column 14 are sent for further processing as desired.

As shown in FIG. 1, the fixed bed trim reactor system provides further hydrogenation of stream 50. This system is typically two reactors with an intercooler but could be a series of reactors with intercoolers between successive reactors. The fixed bed reactor system provides four advantages:

1. The catalytic distillation column no longer needs to operate for high levels of hydrogenation but can be operated for the maximum productivity from the Sud Chemie catalyst, a net ethylene gain with high acetylene, methylacetylene, and propadiene conversion while maintaining acetylene $C_2$ specification.

2. Changes in the catalytic distillation overhead concentration of acetylenics and dienes resulting from catalyst deactivation, carbon monoxide content increase, or feedstock change can be accommodated.

3. Hydrogen removal can be maintained during temporary upsets and/or catalyst deactivation or poisoning thus stabilizing performance of downstream refrigeration systems. If the quantity of hydrogen from the system were to vary, the partial pressures of the downstream distillation system would change and the required quantity of refrigeration would vary. This could create undesirable process upsets.

4. Opportunity is provided for catalyst regeneration by the use of spare fixed bed reactors, thus extending onstream operating life of the entire system.

In addition to control of the temperature and composition profile over the column, it is important to operate with less than complete conversion of the alkynes and dienes over the catalytic distillation column. By doing so, ethylene and propylene gains can be achieved. Further, this operation requires less catalyst than the full hydrogenation of the prior art thus maximizing catalytic distillation catalyst productivity. Operation with a fixed bed reactor system following the column allows this to occur.

If the column were to be operated such that there is no more than approximately 1% ethylene liquid concentration in the reactive beds, hydrogenation in excess of about 95% of the $C_2$ to $C_5$ and heavier dienes can be achieved. This results in from about 5,000 to about 7,500 ppm dienes and acetylenics in the vapor stream 50 from the reflux drum 46 and a minimum ethylene loss of about 1%. To make 100% acetylene conversion, ethylene losses would even be higher. This operation coincides to a hydrogen removal of approximately 30-35% depending upon the feed composition. However, when the overall conversions of the $C_2$ to $C_5$ and heavier dienes and acetylenics are reduced to between approximately 80 and 95% resulting in about 10,000 to about 20,000, and typically about 15,000, ppm $C_2$ to $C_5$ diene and acetylene in the outlet stream 50, ethylene gains can be achieved.

With fixed bed reactors located after the catalytic distillation column 14, and with the catalyst of the invention described above, acetylene breakthrough with about 10,000 to about 55,000, and typically about 20,000, ppm combined $C_3$ and heavier dienes and alkynes can be tolerated from the catalytic distillation column. A typical system with two fixed bed hydrogenation reactors with intercooling has been shown to hydrogenate 100% of the acetylene entering the fixed bed reactor system and approximately 75% of the combined $C_3$ and heavier dienes and alkynes entering the fixed bed reactor system. This results in from about 2500 to about 14,000 and typically only about 5000 ppm breakthrough of dienes and acetylenics from the combined system. This represents approximately 97% hydrogenation of the total $C_2$ and heavier alkynes and diolefins in the feed. Such operation allows for substantial overall ethylene gains of up to about 0.5% with about 70% overall acetylene selectivity toward ethylene at 100% acetylene conversion. This is a substantial improvement over the prior art.

The specific hydrogenation reactivity of ethylene is just slightly lower than the specific reactivity of propadiene. Thus close observation of the $C_3$ diene conversion provides a reliable indication of the stability of the ethylene gain and can be used as a control point for the system. For the catalytic distillation system alone, when $C_3$ diene conversion is between 40 and 60% and typically 45%, ethylene losses are observed. However, when operating at conditions where the $C_3$ diene conversion in the catalytic distillation column is between 10 and 35% and typically about 20%, ethylene gains from about 0.2% to about 0.5% are possible. With the present system, the propadiene conversion can be increased substantially while still maintaining ethylene gain.

During the normal operation of an ethylene unit, variations in the carbon monoxide content of charge gas 10 is typical. In addition, feedstock quality or operating severity may be changed that will impact the acetylene and diolefin content of charge gas. For a fixed catalyst volume in the catalytic distillation column, increases in carbon monoxide or inlet diene and acetylenic concentrations typically result in lower conversion and thus higher releases of these undesired products into stream 50. In the process including a fixed bed reactor system, the temperature of the vapor 50 entering the fixed bed reactor system can be adjusted to either increase or decrease reactivity of the reactor system and thus follow changes in catalytic distillation reaction activity and maintain complete $C_2$ acetylene removal and high hydrogen removal efficiency.

Finally, a fixed bed hydrogenation reactor system is designed to include not only operating reactors but also spares. Catalyst deactivation will occur in both the fixed bed system and the catalytic distillation system. It is not possible to regenerate the catalytic distillation catalyst without shutting down the process or installing a parallel column. Both options are costly. However, a spare fixed bed vapor phase reactor is a relatively inexpensive option. By utilizing a fixed bed reactor system with a spare instead of the single column concept of the prior art, onstream life of the process can be substantially improved.

In the fixed bed hydrogenation system, the net overhead 50 from the catalytic distillation passes through the cross flow heat exchanger 64 and inlet heater 66 into the first fixed bed reactor 68. The effluent from the first reactor 68 goes through the intercooler 70 to the second fixed bed hydrogenation in reactor 72. A series of fixed beds followed by intercoolers can be used in the same fashion in order to achieve the necessary heat transfer when required. The effluent from the last reactor 72 then goes back through the cross flow heat exchanger 64 where heat is extracted and the feed 50 to the fixed bed reactors is heated. The inlet temperature to the fixed bed reactors can be quickly changed to either increase or decrease the extent of hydrogenation in the fixed bed reactors. Such control is necessary to successfully handle changes in carbon monoxide or diene and acetylene feed concentration. Up to a maximum adiabatic temperature rise of 80° F. total for both beds, a stable fixed bed operation with no ethylene loss is possible. A typical adiabatic rise of about 35° F. is expected for normal operation. With an adiabatic temperature rise of from about 70 to about 80 and typically about 80° F., handling of about 35,000 to about 58,000, and typically about 43,000, ppm alkynes and dienes from the catalytic distillation results in from about 9,000 to about 30,000, and typically about 10,000, ppm $C_3$ and heavier dienes and acetylenics in the final product stream 74 while maintaining 100% $C_2$ acetylene conversion primarily to ethylene.

In a similar fashion, the temperature control on the inlet to the fixed bed reactors can provide for compensation for catalyst deactivation providing the typical start-of-run and end-of-run operating temperatures to the fixed bed system. In the prior art, this could only be done by a temperature correction in the catalytic distillation column. This requires a pressure change in the column and thus the fractionation conditions will be altered. With both the catalytic distillation column and fixed bed reactor system of the present invention the catalytic distillation column can operate at constant fractionation conditions and lower temperature corrections for the fixed bed system will be required. This improves system stability and allows for longer life of the catalyst.

FIG. 2 presents an alternate embodiment of the present invention. Instead of catalytic distillation column overhead stream 42 passing to exchanger 44 and then to reflux drum 44, overhead stream 42 is passed directly to cross-flow exchanger 64 and into the fixed bed reactor system. Following the fixed bed reactor system, the effluent is cooled at 65 and the reflux 48 for the column is separated at 67 as a condensed liquid 69 and returned to the column.

Since the stream entering the fixed bed reactor system still contains all of the reflux for the column, the operating temperature of the fixed bed reactors will be somewhat higher to insure complete vapor flow. This will change the design catalyst activity and space velocity to insure stable operation. The advantage of this approach will be a higher mass flow of hydrocarbon that will minimize temperature rise across the fixed beds, a reduced hydrogen partial pressure that will improve selectivity, and a higher space velocity that will both improve selectivity and decrease catalyst costs.

Figure 3:
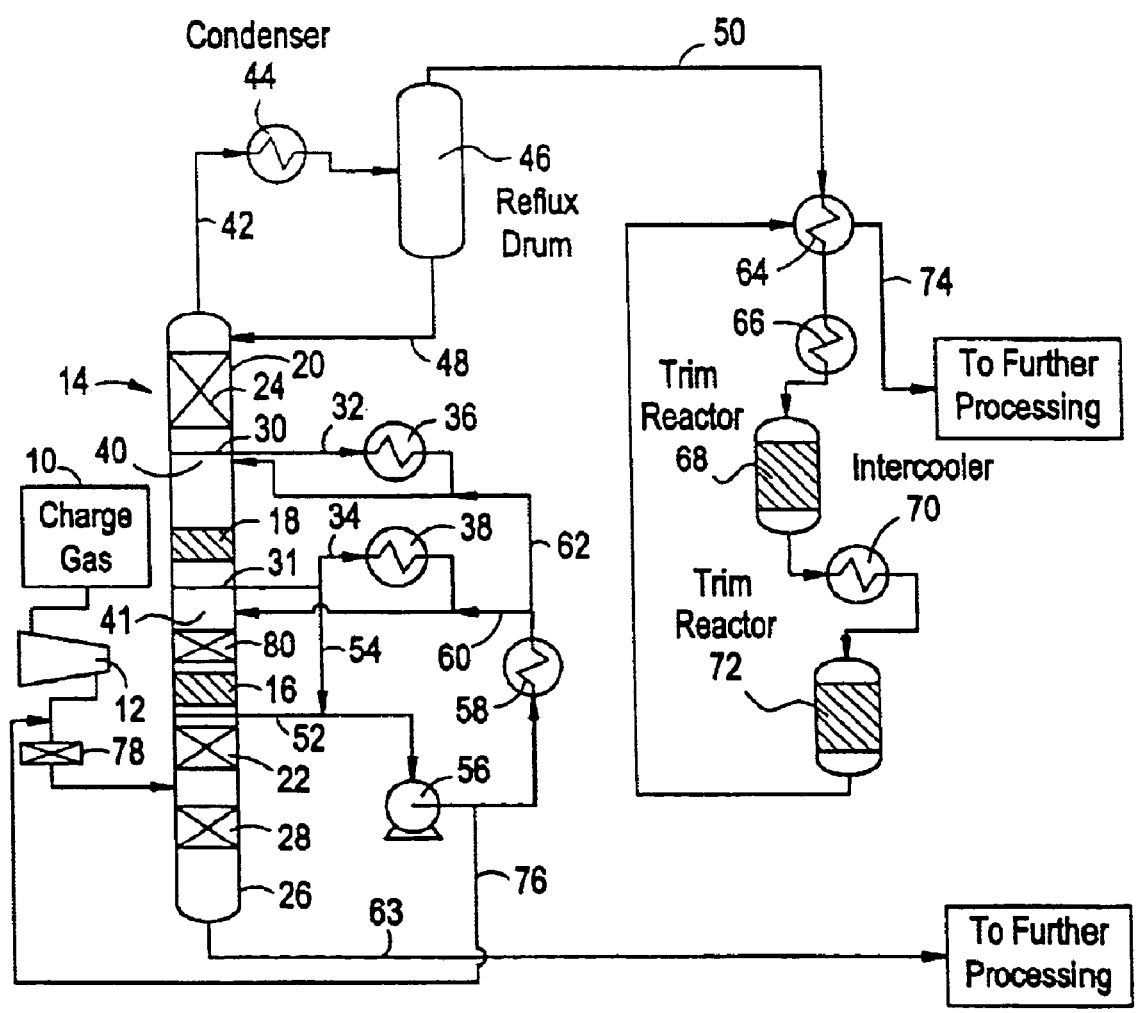
FIG. 3 is a flow diagram of an alternate embodiment of the present invention.

FIG. 3 illustrates an alternate embodiment of the present invention incorporating a pre-reactor. This arrangement is advantageous for bulk selective hydrogenation of feeds high in dienes and alkynes. Following compression at 12 and possible treatment in a guard bed (not shown), the vapor phase feedstock is admixed with recirculation liquid 76 from the pump 56 of column 14 and the two phase mixture passed co-currently through a fixed bed reactor 78. Hydrogenation occurs and the presence of liquid serves to control the temperature rise through vaporization. Hydrogenation reactor 78 can be designed as an operating reactor plus a spare to allow for extending the onstream operation of the system. Following the pre-reactor, the liquid/vapor mixture can be either sent to the column directly as a mixed feed or separated in a separation drum and the liquid and vapor fed separately to the column. The latter is preferred since any oligomers formed in the initial hydrogenation will be in the liquid phase and can be fed to the column below the catalyst beds thus reducing fouling.

Performing the fixed bed hydrogenations before the catalytic distillation column 14 will allow for possibly higher catalyst utilization without experiencing ethylene loss for that portion of the hydrogenation due to the large amount of preferentially absorbed dienes and alkynes of higher reactivity available for hydrogenation. At higher catalyst utilization, lower catalyst volumes would be necessary making the process more economical. A catalytic distillation unit is still required following a pre-reactor to reach hydrogenation specifications. It is anticipated that a maximum of 50% and typically 20% of the hydrogenation duty can be accomplished in the pre-reactor.

Another advantage of a fixed bed hydrogenation reactor before the catalytic distillation column 14 is that the reactor can be used as a guard bed for catalyst poisons. A still further advantage is that the external pre-reactor system could have a spare and thus allow for regeneration without the requirement for shutting the entire plant down for catalyst replacement.

Figure 4:
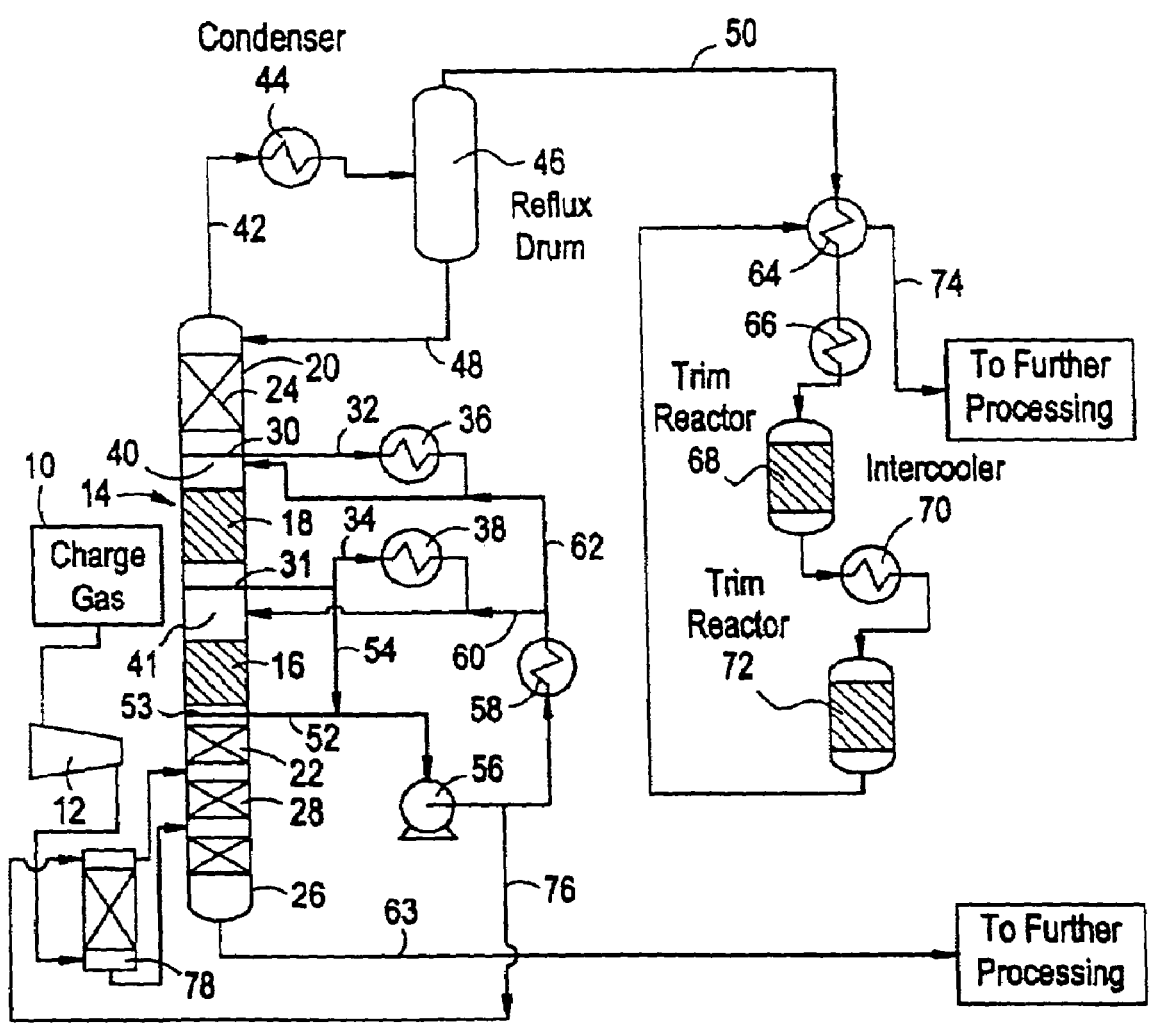
FIG. 4 is a flow diagram illustrating an alternate embodiment of the process of FIG. 3.

Alternately, as shown in FIG. 4, the liquid 76 from pump 56 can flow downwards through the fixed bed 78 and the vapor stream from the compressor 12 can flow upwards. Liquid from the bottom of the fixed bed reactor 78 then flows to a lower portion of column 14 and vapor flows to a higher entry point. The advantage of this counter-current process sequence is that oligomers resulting from polymerization reactions of the unsaturated hydrocarbons are removed from the catalyst bed as formed and do not pass over the remaining portion of the catalyst bed. Also this liquid is sent to column 26 at a lower entry point, minimizing any potential contamination of the catalyst in column 14.

Oligomers which can foul the catalytic distillation catalyst are easily separated and do not rise in the column to contaminate the catalyst. Further, as in the co-current flow option, the pre-reactor catalyst bed can have a spare, allowing for regeneration while the rest of the system is operating. The ability to easily regenerate on-line will increase system cycle lengths as the catalyst zone at the feed inlet is expected to have the highest fouling rate.

To minimize fouling in the fixed bed pre-reactor, liquid flow rates need to be sufficient to minimize local hot spots due to the high heat of hydrogenation and to wash any oligomers formed off the catalyst. The operation of these beds is preferably in the vapor continuous zone. For cracked gas feeds that exhibit extreme fouling tendencies, operating in the liquid continuous zone is also possible.

Figure 5:
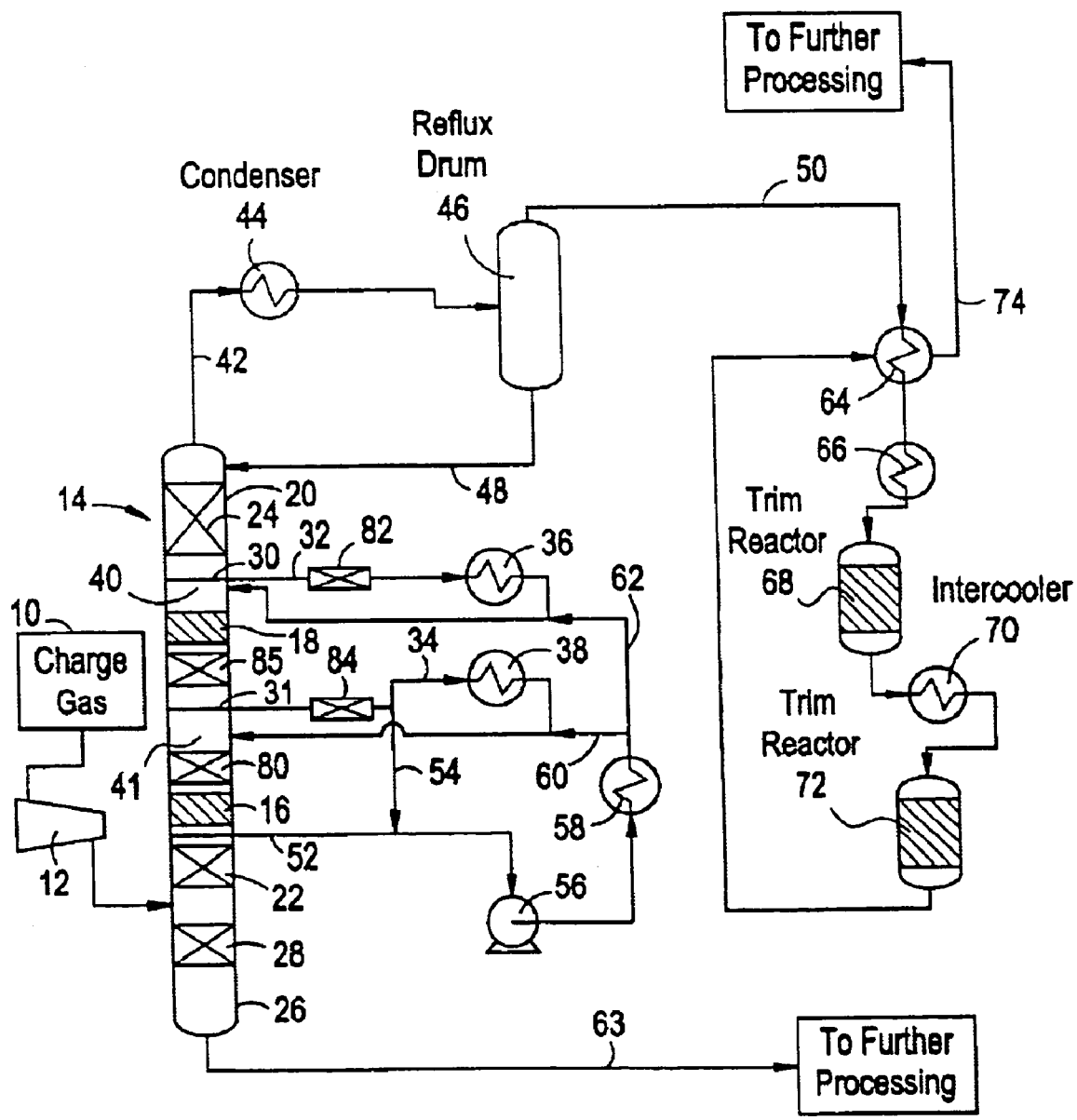
FIG. 5 is a flow diagram similar to FIG. 1 but illustrating an alternate embodiment of the present invention; and, FIG. 6 is a flow diagram illustrating a vapor phase front end system embodiment of the invention.

FIG. 5 illustrates a further embodiment of the present invention which incorporates fixed bed reactors within the liquid pumparound or intercooler streams that are withdrawn from the column 14. The fixed bed hydrogenation reactors 82 and 84 are placed in the side stream from collecting tray 30 and the side stream from collecting tray 31, respectively. These fixed beds 82 and 84 are in addition to the reactive hydrogenation sections 16 and 18 in the hydrogenation sections 16 and 18 in the catalytic distillation column 14. A mass transfer zone 85 in the form of structured packing or trays is also added above the withdrawal point and below the catalyst bed. This zone allows for hydrogen to be saturated into the liquid phase and thus provide the hydrogen required for the hydrogenation of the alkynes and dienes in the withdrawn liquid.

The ability of the present invention to remove from about 30 to about 40% of the hydrogen from the charge gas prior to chilling and condensation steps lowers the energy consumption and reduces capital cost. The ability to hydrogenate 100% of the acetylene irrespective of the carbon monoxide concentration without any $C_2$ or $C_3$ olefin losses was not possible with the prior art. The combined fixed bed and catalytic distillation steps provide superior handling of system upsets while maintaining stable diene/alkyne hydrogenation and hydrogen removal.

Figure 6:
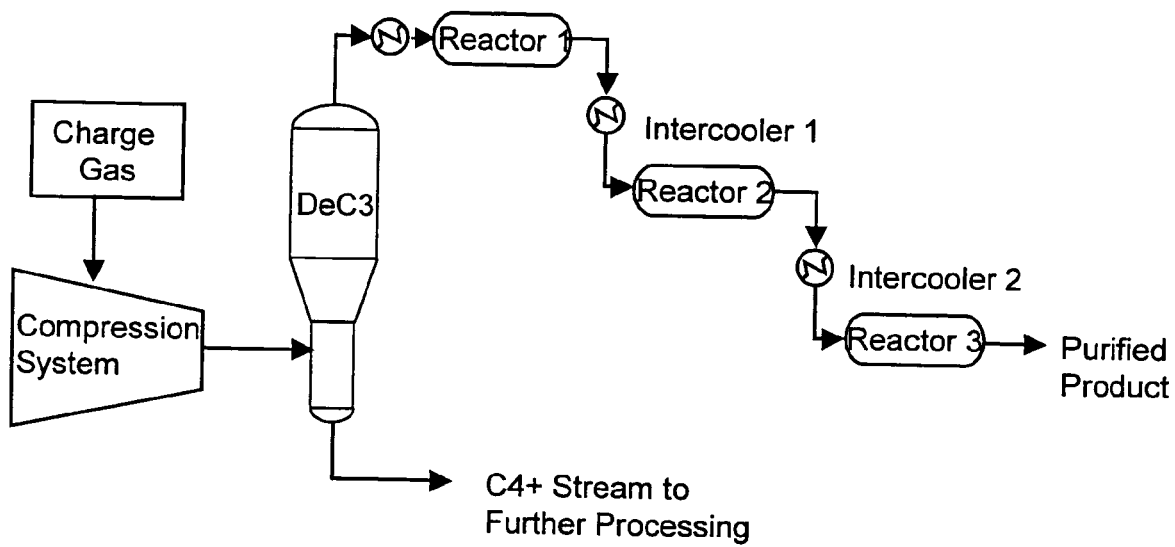

FIG. 6 illustrates a vapor phase front end system embodiment of the present invention.

In a conventional front-end selective catalytic hydrogenation reactor system, the acetylene reactors precede the demethanizer in the process. There are two options in current practice. One is a front end de-ethanizer and the other is a front end de-propanizer. In the front-end de-ethanizer design variation, the de-ethanizer is the first distillation column and the reactors are on the overhead stream. Thus, the feed contains a C2 and lighter stream. Similarly, in a front-end depropanizer unit, the initial distillation column is the depropanizer. As the acetylene reactors are used to treat the overhead of this column, the feed to the reactors is composed of $C_3$ and lighter hydrocarbons. The reactor system is a combination of reactors with an intercooler between each reactor pair. The intercoolers are used to limit the temperature rise and achieve the required selectivity, i.e. limit the ethylene loss to ethane.

In the conventional de-ethanizer and depropanizer designs, $C_2$ and higher dienes have to be limited to a low amount, typically less than about 10,000 ppm. Importantly, there can be minimal amounts of any $C_4$ acetylenes or dienes in the overhead product. These would be present in the feed as a result of less than perfect separation. Using conventional catalysts, this low feed level of total dienes and acetylenics is required in order to achieve 100% acetylene conversion without excessive reactor temperature rise. Note that the primary objective is to remove acetylene to levels of <1 ppm in the outlet. The conversion of higher hydrocarbon acetylenes and dienes does not necessarily have to be essentially 100%. However, the higher the conversion, the more process advantages result. Since hydrogen and olefins are in excess in these feeds, catalyst selectivity is important. The reaction of olefins with hydrogen represents a loss in selectivity, for example, ethylene loss to ethane or propylene loss to propane. In addition these reactions will cause additional heat generation due to the exothermic heat of reaction. In these reactions, the total hydrogen conversion indicates the total reaction and hence the heat generated.

Excessive heat generation (in any reactor before intercooling) will lead to excessive temperature rises across the reactor, which in turn leads to temperature runaways. In practice, the temperature rise across any reactor is limited. If the system is operated with a low temperature rise, selectivity is improved since the extent of reaction or hydrogen conversion is limited. For a given hydrogen conversion this will require more reactors than if the design temperature rise is higher. Higher temperature rise across any reactor will allow non-selective reactions to occur with greater frequency. Thus a designer optimizes the number of reactors against loss of selectivity. While it is possible to hydrogenate higher levels of acetylenes and dienes in conventional vapor phase systems when using conventional catalysts, a large number of costly reactors and intercoolers have to be used to avoid runaways and/or selectivity losses. For feedstocks with more than 10,000 ppm total acetylenes and dienes and especially if the initial fractionation system was a de-butanizer and the resultant feed contained $C_4$ and lighter alkynes and dienes in excess of 20,000 ppm, three or more reactor systems are required.

In the current improved process (FIG. 6), the compression system is followed by a distillation tower which operates as a de-propanizer. The bottom product containing $C_4$'S and higher hydrocarbons is further processed in order to remove the $C_4$ and higher dienes and alkynes usually with a combination of trickle bed reactors and distillation columns.

The overhead of the depropanizer tower product which includes $C_2$ acetylene as well as methylacetylene and propadiene, totaling more than about 10,000 ppm, can be treated with a series of front end reactors loaded with the improved SCI catalyst. While in FIG. 6, a series of 3 fixed bed vapor phase reactors with intercooling has been shown, in many case, due to the improved catalyst selectivity, processing can take place with less than three reactors and two intercoolers. With this reactor system $C_2$ and $C_3$ dienes and alkynes can be removed without ethylene or propylene losses and without temperature runaways as a result of the higher vapor phase selectivity at equivalent hydrogen conversions (or heat generation).

The following examples illustrate aspects of the invention as well as comparisons between the catalyst used in the process of invention and the use of commercially available catalysts. Examples 1-10 illustrate a gas phase operation process and Examples 11-14 illustrate a liquid phase operation.

EXAMPLE 1 (COMPARATIVE)

This is a comparison example demonstrating the properties of a commercially available catalyst that is not within the scope of the invention. The commercially available catalyst can be obtained from Süd-Chemie Inc. of Louisville, Ky. under the product name of G-83C. Analysis shows that the catalyst contains 0.018 weight percent of palladium and 0.07 weight percent of silver on an alumina carrier. The carrier for the catalyst has a BET surface area of about 4.3 $m^2/g$. The catalyst has a total pore volume of 0.295 cc/g and a pore volume distribution in Å as follows:

| Pore Diameter in Å | Percentage of total pore volume |
|---|---|
| 35.6-100.0 | 0.00% |
| 100.0-300.0 | 0.10% |
| 300.0-500.0 | 0.07% |
| 500.0-1000.0 | 0.27% |
| Above 1000.0 | 99.56% |

EXAMPLE 2

This example illustrates the preparation and properties of the Sud Chemie catalyst used in the process of the present invention. The catalyst is prepared by immersing 25 grams of commercially available alumina spheres (size) with a BET surface area of about 3.5 $m^2/g$ using the nitrogen method in a palladium chloride solution of sufficient concentration to yield a palladium loading of 0.018 weight percent with a palladium depth of penetration controlled to wherein at least about 90 percent of the palladium is within about 250 microns of the surface of the spheres. After palladium impregnation, the catalyst is calcined at 250° C. for about 3 hours. The catalyst is then wet reduced in a 5 percent aqueous sodium formate solution heated to a temperature of about 170° F. (76° C.) for about one hour. The catalyst is then washed free of chlorides (less than 100 ppm) with deionized water at about 160° F. (71° C.). The catalyst is then dried at about 250° F. (121° C.) for about 18 hours. The palladium containing precursor catalyst is then impregnated with silver by dipping the catalyst spheres in a silver nitrate solution of sufficient concentration to yield a silver loading of 0.05 weight percent. The catalyst is then calcined at 454° C. for three hours. The resulting catalyst has a total pore volume of 0.519 cc/g and a pore volume distribution in Å as follows:

| Pore Diameter in Å | Percentage of total pore volume |
|---|---|
| 35.6-100 | 0.00% |
| 100.0-300.0 | 0.10% |
| 300.0-500.0 | 0.27% |
| 500.0-1,000.0 | 1.71% |
| Above 1,000.0 | 97.93% |

EXAMPLES 3 (COMPARATIVE) AND 4

The Sud Chemie catalyst of Example 2 was placed in a metal tube reactor and tested under gas phase hydrogenation conditions. Gas samples of the feed and product were collected at specified time intervals in sample bags and analyzed off-line by Gas Chromatography. Total pressure in the reactor was kept at 150 psig. Typical GHSV used was 5500. The temperature range tested was 140° F. to 1900° F. The catalysts tested were (1) the commercial front end palladium/silver on alumina catalyst of comparative Example 1, and (2) the catalyst of the invention of Example 2.

The feed composition in gas phase is given in Table 1. This feed represents normal CO level as well as high diolefin and acetylenic loads (35,000 ppm of total dienes and alkynes).

TABLE 1

Example I Gas Phase Feed Composition

| Component | Volume (%) |
|---|---|
| $H_2$ | 18.20 |
| $N_2$ | 26.26 |
| CO | 0.06 |
| Ethylene | 28.55 |
| Acetylene | 0.07 |
| Propane | 0.22 |
| Propylene | 17.83 |
| Methylacetylene (MA) | 0.40 |
| Propadiene (PD) | 0.28 |
| N-butane | 0.04 |
| 2-Butenes | 0.95 |
| 1-Butene | 5.89 |
| 1,3-Butadiene (BD) | 0.93 |
| Isoprene | 0.31 |

Results showing the comparative performance between the conventional catalyst, G83-C (Comparative Example 3), and the Sud Chemie catalyst employed in the process of the invention (Example 4) are provided in Table 2.

TABLE 2

600 ppm CO Results

| | Example 3 (Comp.) | Example 4 |
|---|---|---|
| Catalyst Type | G83-C | |
| Weight (g) | 0.5 | 0.5 |
| Bed Temperature (F.) | 176 | 176 |
| Reaction Pressure (Psig) | 150 | 150 |
| GHSV (hr-1) | 5359 | 5338 |
| Acetylene % Conversion | 93.56 | 100.00 |
| Ethylene % Gain/Loss | −2.60 | −0.89 |
| Acetylene % Selectivity to Ethylene | −998 | −343 |
| Propadiene % Conversion | 61.80 | 51.82 |
| Methylacetylene % Conversion | 83.28 | 92.41 |
| MA/PD % Selectivity to propylene | 91 | 93 |
| Butadiene % Conversion | 82.43 | 96.31 |
| Butadiene % Selectivity to Butenes | 95 | 98 |
| Isoprene % Conversion | 72.11 | 99.24 |
| Rate-$H_2$ conv., lb-mol/h/lb cat | 0.0047 | 0.0057 |
| Hydrogen Conversion | 12.47 | 11.37 |
| Inlet Composition | | |
| ppm wt Acetylene | 655 | 654 |
| ppm wt Propadiene | 3860 | 3815 |
| ppm wt Methylacetylene | 5483 | 5548 |
| ppm wt Butadiene | 17258 | 17237 |

TABLE 2-continued 600 ppm CO Results

| | Example | |
|---|---|---|
| | 3 (Comp.) | 4 |
| ppm wt $C_5$ dienes | 7274 | 7125 |
| Total ppm wt. (acetylene + dienes) | 34531 | 34379 |
| Outlet Composition | | |
| ppm wt Acetylene | 42 | 0 |
| ppm wt Propadiene | 1475 | 1838 |
| ppm wt Methylacetylene | 917 | 421 |
| ppm wt Butadiene | 3032 | 637 |
| ppm wt $C_5$ dienes | 2028 | 54 |
| Total ppm wt. (acetylene + dienes) | 7494 | 2950 |

A comparison of the results from Comparative Example 3 and Example 4 shows that at 176° F. the acetylene conversion of the improved catalyst (Example 4) is higher than the conventional catalyst (Comparative Example 3) with much lower losses of ethylene. This occurs at even a lower net overall hydrogen conversion. Thus, Example 4 would show a higher selectivity at a lower heat generation. This permits the use of fewer reactors if desired. At this temperature, the catalyst of Example 4 made acetylene specification of 0 ppm with less than 1% ethylene loss while the conventional catalyst of Comparative Example 3 allowed 42 ppm of acetylene in the product with 2.6% ethylene loss.

The advantage of the improved catalyst is either the higher reactivity (hydrogen conversion) at the same selectivity of the $C_3$, $C_4$ and $C_5$ dienes at similar acetylene conversions or the higher selectivity at the same conversion (Table 2). Example 4 data show about 3,000 total outlet ppm of the higher dienes compared to about 7,500 outlet ppm for the conventional catalyst (Example 3). Since the hydrogen conversion for Example 4 is in fact lower, this translates into much higher selectivity. This provides an advantage for the catalytic distillation with trim reactor applications where more than 10,000 ppm of higher alkynes and dienes are present in the feed along with the acetylene. The advantage of using a catalyst with such higher $C_3$, $C_4$ and $C_5$ reactivity is that the acetylene-free product will require lesser processing or may not require any further processing steps to purify from $C_3$, $C_4$ and $C_5$ dienes and acetylenic impurities.

The improved catalyst provides a wider temperature window of operation than the Example 3 catalyst. The window of operation is defined as the difference between the temperature where there are significant ethylene losses and the initial temperature where acetylene specification is achieved. Reaction temperature is used commercially in these type of systems as the main control parameter to keep making on spec product through periods of feed composition variation. Temperature is also raised during CO spikes and during the duration of the run as the catalyst deactivates in order to keep product spec. It is very important to use a catalyst with a wide window of high acetylene selectivity to ethylene so that the product quality can be consistent. In addition, when the temperature is raised and the ethylene to ethane hydrogenation reaction is preferred, temperature runaways can result from a narrow temperature window catalyst. The temperature window of the Example 4 catalyst is much wider than that of the catalyst employed in Example 3. Thus, the data show that the improved catalyst of Example 4 can be used at up to 176° F. with minimum losses but the catalyst of Example 3 cannot be used at that temperature without making off-specification product.

EXAMPLES 5 (COMPARATIVE) AND 6

In addition to the low CO feed, a high CO feed simulating a CO spike condition was used for some of the experiments. The only difference between the high CO feed and the feed in Table 1 is that the CO is 0.12% on a volumetric basis. Total pressure in the reactor for all gas phase experiments was kept at 150 psig. The temperature range tested was 140 to 190° F. Results showing the comparative performance between conventional catalyst G83-C and the improved catalyst as provided in Table 3 below, wherein Example 6 illustrates the invention and Example 5 is presented for comparison purposes and is outside the scope of the invention.

TABLE 3

1,200 ppm CO Results

| | Example | |
|---|---|---|
| | 5 (Comp.) | 6 |
| Catalyst Type | Comp. Example 1 | Catalyst of Example 2 |
| Weight (g) | 0.52 | 0.50 |
| Bed Temperature (° F.) | 185 | 185 |
| Reaction Pressure (psig) | 150 | 150 |
| GHSV (hr$^{-1}$) | 5348 | 3890 |
| Acetylene % Conversion | 96.50 | 100.00 |
| Ethylene % Gain/Loss | −6.80 | −0.48 |
| Acetylene % Selectivity to Ethylene | −2992 | −192 |
| Propadiene % Conversion | 70.00 | 34.00 |
| Methylacetylene % Conversion | 86.52 | 94.93 |
| MA/PD % Selectivity to propylene | 78 | 92 |
| Butadiene % Conversion | 84.62 | 98.33 |
| Butadiene % Selectivity to Butenes | 89 | 98 |
| Isoprene % Conversion | 71.95 | 94.07 |
| Rate-H$_2$ conv., lb-mol/h · lb$_{cat}$ | 0.0065 | 0.0031 |
| Hydrogen conversion | 17.42 | 8.01 |
| Inlet Composition | | |
| ppm wt Acetylene | 607 | 607 |
| ppm wt Propadiene | 3860 | 3860 |
| ppm wt Methylacetylene | 5530 | 5530 |
| ppm wt Butadiene | 13214 | 13214 |
| ppm wt $C_5$ dienes | 3308 | 3308 |
| Total ppm wt. (acetylene + dienes) | 26519 | 26519 |
| Outlet Composition | | |
| ppm wt Acetylene | 21 | 0 |
| ppm wt Propadiene | 1159 | 2548 |
| ppm wt Methylacetylene | 746 | 280 |
| ppm wt Butadiene | 2032 | 221 |
| ppm wt $C_5$ dienes | 928 | 196 |
| Total ppm wt. (acetylene + dienes) | 4886 | 3245 |

The high CO performance at higher temperature is important since during the periodic CO spikes temperatures will be raised in order to achieve the desired acetylene specification. At the end of the CO spike before temperature can be reduced there is high probability for temperature runaways. Catalysts with wide temperature windows which overlap between periods of low and high CO are ideal for CO tolerant performance. Table 3 shows that the improved catalyst made acetylene spec at 185° F. while the conventional catalyst still allowed 21 ppm acetylene in the outlet. The selectivity of acetylene to ethylene was higher for the catalyst system of Example 6 than that obtained with the catalyst of Example 5, the latter resulting in 6.8% ethylene losses of less than 1%. The example also shows that the hydrogen conversion for the conventional catalyst was over 17% compared to 8% for the catalyst of the process. The high conversion for the conventional case reflects the high loss of ethylene to ethane and represents not only an economic penalty but a potential runaway situation due to the high amount of heat generated.

At the same time the improved catalyst again provided much lower total $C_3$, $C_4$ and $C_5$ dienes and acetylenics in the outlet (3,200 ppm versus 4,900 ppm for G83-C) making it a superior catalyst for this application. At this higher temperature and CO level, the MA/PD selectivity to propylene for the catalyst of Example 6 is 92% compared to 78% for the catalyst of Example 5. Also the butadiene selectivity to butenes for the Example 6 catalyst is 98% compared to 89% of the Example 5 catalyst. Both of these selectivities of dienes and acetylenics to olefins are important for the product quality since olefin (propylene and butene) losses lead to loss of valuable product.

EXAMPLES 7 TO 10

In these examples, no acetylene or CO were used in the feed. Table 4 sets forth the feed composition. Total pressure in the reactor for these experiments was kept at 60 psig and GHSV used were in the 30,000-200,000 range. The temperature range tested was 140° F. to 200° F. The catalysts tested were the commercial front end G83-C catalyst (Comparative Example 1) and the Sud Chemie catalyst employed in the process of the invention (Example 2). Results showing the comparative performance between conventional catalyst G83-C and the improved catalyst are provided in Table 5 below wherein Examples 8 and 10 illustrate the invention and Examples 7 and 9 are presented for comparison purposes and are outside the scope of the invention.

TABLE 4

Gas Phase Feed Composition

| Component | Volume % |
| --- | --- |
| $H_2$ | 11.38 |
| Methane | 77.54 |
| Acetylene | 0.00 |
| Ethylene | 3.83 |
| Propadiene | 0.13 |
| Methylacetylene | 0.23 |
| Propylene | 3.23 |
| Propane | 0.07 |
| 1,3-Butadiene | 0.93 |
| 1-Butene | 1.06 |
| 2-Butenes | 0.67 |
| n-Butane | 0.04 |
| Isoprene | 0.89 |

TABLE 5

0 ppm CO

| | Example | | | |
| --- | --- | --- | --- | --- |
| | 7 (Comp.) | 8 | 9 (Comp.) | 10 |
| Catalyst Type | Comp. Example 1 | Example 2 | Comp. Example 1 | Example 2 |
| Weight (g) | 0.43 | 0.50 | 0.43 | 0.21 |
| Bed Temperature (° F.) | 144 | 145 | 203 | 202 |
| Reaction Pressure (psig) | 60 | 60 | 60 | 60 |
| GHSV ($hr^{-1}$) | 109,000 | 33,402 | 204,000 | 80,336 |
| Ethylene % Gain/Loss | −33.17 | −12.47 | −40.32 | −27.78 |
| Propadiene % Conversion | 84.74 | 96.44 | 77.85 | 83.12 |
| Methylacetylene % Conversion | 80.39 | 94.25 | 74.00 | 83.12 |
| Methylacetylene/Propadiene % Selectivity to propylene | −110.00 | −79.00 | −14.00 | −19.00 |
| Butadiene % Conversion | 77.04 | 93.73 | 69.59 | 79.36 |
| Butadiene % Selectivity to Butenes | 68.00 | 90.10 | 55.00 | 77.00 |
| Isoprene % Conversion | 68.50 | 89.95 | 56.33 | 75.30 |
| rate-$H_2$ conv., lb-mol/h/$lb_{cat}$ | 0.07 | 0.07 | 0.17 | 0.18 |
| Hydrogen conversion | 31.55 | 30.12 | 36.30 | 36.46 |
| Kinetic Selectivity Ratio of Butadiene vs. ethylene | 3.6 | 20.8 | 2.3 | 4.8 |
| Kinetic Selectivity Ratio of Methylacetylene vs. ethylene | 4.7 | 25.0 | 2.9 | 5.5 |
| Kinetic Selectivity Ratio of Propadiene vs. ethylene | 4.0 | 21.4 | 2.6 | 5.5 |
| Kinetic Selectivity Ratio of isoprene vs. ethylene. | 2.9 | 17.3 | 1.6 | 4.3 |
| Inlet Composition | | | | |
| ppm wt Acetylene | 0 | 0 | 0 | 0 |
| ppm wt Propadiene | 1306 | 1474 | 1333 | 1411 |
| ppm wt Methylacetylene | 2272 | 2428 | 2320 | 2424 |
| ppm wt Butadiene | 9319 | 11117 | 9516 | 11230 |
| ppm wt $C_5$ dienes | 8912 | 16210 | 9100 | 16562 |
| Total ppm wt. (acetylene + dienes) | 21809 | 30905 | 22194 | 31370 |
| Outlet Composition | | | | |
| ppm wt Acetylene | 0 | 0 | 0 | 0 |

TABLE 5-continued 0 ppm CO

| | Example | | | |
|---|---|---|---|---|
| | 7 (Comp.) | 8 | 9 (Comp.) | 10 |
| ppm wt Propadiene | 352 | 90 | 696 | 270 |
| ppm wt Methylacetylene | 521 | 92 | 1104 | 439 |
| ppm wt Butadiene | 2975 | 743 | 5441 | 2432 |
| ppm wt c5 dienes | 4155 | 1736 | 6568 | 4140 |
| Total ppm wt. (acetylene + dienes) | 8003 | 2661 | 13809 | 7281 |

Examples 7 and 8 provide a comparison between G83-C and the catalyst employed in the process of the invention at about 145° F. Examples 9 and 10 provide a similar comparison at the higher temperature of about 202° F. At both temperature levels G83-C and the catalyst of the invention have similar overall catalyst productivities: 0.07 lb-moles $H_2/lb_{cat}/h$ at 145° F. and 0.17 IB moles $H_2/lb_{cat}/h$ at 202° F. This is also reflected in nearly the same hydrogen conversion levels. However, the selectivities of the catalysts for the desired reactions, i.e., the hydrogenations of $C_3$, $C_4$ and $C_5$ dienes and acetylenics, versus the undesired competing parallel reaction of ethylene hydrogenation, as expressed by the Kinetic Selectivity Ratio, differ significantly. The kinetic selectivity ratio of Butadiene (BD) vs. ethylene (ETH) is calculated as $\ln(1-X_{BD})/\ln(1-X_{ETH})$, where $X_{BD}$ and $X_{ETH}$ are the fractional conversions of butadiene and ethylene respectively. The higher the ratio of kinetic selectivity ratio of butadiene versus ethylene, the more selective is the catalysis for the desired hydrogenation of butadiene over ethylene.

Based on the results from Table 5, the two catalysts exhibit significantly different selectivities. The catalyst of the invention showed a ratio of 20.8 compared to 3.6 for G83-C at 140° F. The ratio for the improved catalyst was 4.8 compared to 2.3 of G83-C at 202° F. Similar trends were observed for the selectivity ratios of methyl acetylene, propadiene and isoprene compared to ethylene, with the selectivity of the catalyst of the invention being higher than that of G83-C in all cases. This comparison shows that in the absence of acetylene, the improved catalyst shows higher reactivity for the $C_3$, $C_4$ and $C_5$ dienes and acetylenics compared to ethylene. This shows that the selectivity advantage for the catalytic distillation with trim reactor applications that the improved catalyst provides spans the full range of possible CO and alkyne compositions.

EXAMPLES 11-14

These examples illustrate a liquid phase operation employing a known catalyst, designated G68-I of Sud Chemie, and the Sud Chemie catalyst of Example 2. Catalyst G68-I contains 0.2 wt. % palladium and 0.1 wt. % silver on alumina and is supplied as 2.5 mm extruded pellets.

The liquid phase feed was a mixture of $C_3$'s, $C_4$'s and $C_5$'s saturated with hydrogen. A predetermined amount of ethylene was also added to this mixture before the feed was passed over the catalyst bed. A typical feed composition is provided in Table 6. Gas samples of the feed and product were collected at specified time intervals in sample bags and analyzed off-line by gas chromatography. Total pressure in the reactor was maintained at 500 psig which is a sufficiently high level to keep the mixture in the liquid phase. The test temperature was 180° F.

TABLE 6

| Component | Typical feed mole % |
|---|---|
| Hydrogen | 1.72 |
| Ethylene | 2.53 |
| Propane | 0.34 |
| Propylene | 0.30 |
| Propadiene | 0.03 |
| Methylacetylene | 0.07 |
| Isobutane | 92.11 |
| n-Butane | 0.05 |
| t-2-Butene | 0.23 |
| 1-Butene | 0.61 |
| c-2-Butene | 0.37 |
| 1,3 Butadiene | 0.55 |
| Isoprene | 1.07 |
| 2me-2butene | 0.02 |

Results showing the comparative performance between catalyst G68-I and the catalyst of the invention (Example 2) are provided in Table 7 below wherein Examples 12 and 14 illustrate the process of the invention and Examples 11 and 13 are presented for comparison purposes and are outside the scope of the invention

TABLE 7

| | Example | | | |
|---|---|---|---|---|
| | 11 (Comp.) | 12 | 13 (Comp.) | 14 |
| Catalyst type | G68-I | Example 2 | G68-I | Example 2 |
| Weight (g) | 0.50 | 0.5005 | 0.5 | 0.5005 |
| Bed temp. (° F.) | 178 | 180 | 179.60 | 181 |
| Reaction Pressure | 500 | 500 | 500.00 | 500 |

TABLE 7-continued

|  | Example | | | |
| --- | --- | --- | --- | --- |
|  | 11 (Comp.) | 12 | 13 (Comp.) | 14 |
| (psig) | | | | |
| WHSV ($hr^{-1}$) | 677 | 955 | 363 | 568 |
| $H_2$ to (dienes + acetylenes) stoichiometric inlet molar ratio | 1.36 | 1.28 | 0.49 | 0.51 |
| Ethylene conversion (%) | 24.09 | 25.29 | 9.68 | 3.10 |
| Hydrogen conversion (%) | 61.66 | 68.92 | 61.67 | 80.90 |
| Methyl acetylene conversion (%) | 51.67 | 64.70 | 48.93 | 61.51 |
| Propadiene conversion (%) | 38.25 | 55.22 | 30.46 | 50.38 |
| Methylaceylene/propadiene % selectivity to propylene | −30 | 24 | 34 | 90 |
| Butadiene conversion (%) | 39.17 | 56.01 | 35.41 | 46.08 |
| Butadiene selectivity to butenes | 73 | 91 | 94 | 99 |
| Isoprene conversion (%) | 32.47 | 45.76 | 27.75 | 28.86 |
| Rate $H_2$ conversion (Lb-mol $H_2$/h/$lb_{cat}$) | 0.089 | 0.248 | 0.072 | 0.152 |
| Kinetic selectivity ratio of butadiene vs. ethylene | 1.80 | 2.82 | 4.29 | 19.64 |
| Kinetic selectivity ratio of methyl acetylene vs ethylene | 2.64 | 3.57 | 6.60 | 30.37 |
| Kinetic selectivity ratio of propadiene vs. ethylene | 1.75 | 2.76 | 3.57 | 22.29 |
| Kinetic selectivity ratio of isoprene vs. ethylene | 1.42 | 2.10 | 3.19 | 10.83 |
| Inlet Composition | | | | |
| Hydrogen | 1.67 | 2.27 | 1.69 | 2.00 |
| Ethylene | 1.24 | 2.08 | 0.71 | 3.76 |
| Propylene | 0.47 | 0.61 | 0.26 | 0.90 |
| Propadiene | 0.02 | 0.02 | 0.02 | 0.05 |
| Methyl acetylene | 0.00 | 0.02 | 0.01 | 0.05 |
| Isobutane | 94.12 | 91.81 | 90.67 | 86.50 |
| Butenes | 0.95 | 1.12 | 2.72 | 2.61 |
| 1,3-Butadiene | 0.42 | 0.52 | 0.86 | 1.32 |
| Isoprene | 0.78 | 1.21 | 2.87 | 2.4916 |
| Outlet Composition | | | | |
| Hydrogen | 0.64 | 0.72 | 0.65 | 0.38 |
| Ethylene | 0.89 | 1.57 | 0.65 | 3.66 |
| Propylene | 0.43 | 0.61 | 0.26 | 0.97 |
| Propadiene | 0.01 | 0.01 | 0.01 | 0.02 |
| Methyl acetylene | 0.00 | 0.01 | 0.00 | 0.02 |
| Isobutane | 95.22 | 93.33 | 92.17 | 88.30 |
| Butenes | 1.07 | 1.40 | 3.04 | 3.28 |
| 1,3-butadiene | 0.27 | 0.23 | 0.55 | 0.71 |
| Isoprene | 0.56 | 0.67 | 1.83 | 1.79 |

Experiments 11 and 12 provide a comparison between the performance of G68-I and the improved catalyst at high hydrogen to diene and acetylenic molar ratio of 1.3. Experiments 13 and 14 provide a similar comparison at the a lower ratio of 0.5. The improved catalyst showed much higher catalyst productivity in the liquid phase compared to the conventional catalyst. At the high hydrogen stoichiometric ratio the improved catalyst showed a productivity of 0.248 compared to 0.089 lb-mol $H_2/h^{-1}/lb_{cat}$ for the conventional catalyst. Similarly at the lower hydrogen stoichiometric ratio the improved catalyst productivity is 0.152 compared to 0.072 lb-mol $H_2/h^{-1}/lb_{cat}$ for the conventional catalyst. The improved productivity represents increased activity for the improved catalyst under equivalent conditions. The improved catalyst further allows the use of a lower amount of catalyst thus saving capital costs for the process.

In terms of selectivity of the improved catalyst, it clearly provides an advantage over catalyst G68-I. The Kinetic Selectivity Ratio is used here to express the catalyst selectivity for the desired reactions, i.e., the hydrogenations of $C_3$, $C_4$ and $C_5$ dienes and acetylenics, versus the undesired competing parallel reaction of ethylene hydrogenation.

Based on the results from Table 6, the improved catalyst showed higher ratios compared to the ratios of the catalyst G68-I for all conditions and all competing reactions (MA, PD, BD and isoprene). In particular for Example 14 (improved catalyst, low hydrogen stoichiometric ratio) the BD to ethylene kinetic selectivity ratio is 20, for MA 30, for PD 22 and for isoprene 11. These ratios can be contrasted to the maximum ratio achieved for the catalyst G68-I which is 6.6.

In addition to the higher reactivity of this catalyst to $C_3$, $C_4$ and $C_5$ dienes and acetylenics, the improved catalyst is more selective for diene hydrogenation to olefins compared to the catalyst G68-I. Comparing Examples 11 and 12 shows the improved catalyst has a MA/PD selectivity to propylene of 24% compared to the −30% for the catalyst G68-I. The selectivity of BD to butenes is 91% for the improved catalyst compared to 73% for catalyst G68-I. Similarly comparing between Examples 11 and 12 shows MA/PD selectivity of 90% for the improved catalyst compared to 34% for the catalyst G68-I. Similarly, the selectivity of BD to butenes is 99% for the improved catalyst compared to 94% for the catalyst G68-I.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

The invention claimed is:

1. A process for the selective hydrogenation of alkyne and/or diene present in an olefin-containing hydrocarbon feed, the process comprising contacting the hydrocarbon feed containing at least about 10,000 ppm by weight alkyne and/or diene content with a catalyst in a first reaction zone under selective hydrogenation conditions, said catalyst including palladium and at least one Group IB metal incorporated into an inorganic support, wherein the support has a surface area of from about 2 to about 20 $m^2/g$ and a pore volume greater than about 0.4 cc/g, at least about 90% of the pore volume is contained in pores with pore diameters larger than about 500 Å, and the pore volume of the pores with a pore diameter from about 500 Å to about 1,000 Å comprises from about 1% to about 2% of the total pore volume.

2. The process of claim 1 wherein the catalyst includes from about 0.01 to about 0.1 weight percent palladium and from about 0.005 to about 0.6 weight percent of Group IB metal, the weight ratio of the Group IB metal to the palladium ranging from about 0.5:1 to about 6:1.

3. The process of claim 2 wherein the Group IB metal is silver.

4. The process of claim 1 wherein the alkyne includes acetylene.

5. The process of claim 1 wherein the olefin includes ethylene.

6. The process of claim 1 wherein the selective hydrogenation conditions include a temperature of from about 60° F. to about 200° F., a pressure of from about 100 psig to about 250 psig, and a space velocity of from about 1,000 to about 5,000 GHSV.

7. The process of claim 1 wherein the first reaction zone comprises a catalytic distillation unit.

8. The process of claim 7 further comprising removing a vapor phase overhead from the catalytic distillation unit.

9. The process of claim 8 wherein at least a portion of the vapor phase overhead is introduced into a second reaction zone under selective hydrogenation reaction conditions in the presence of said catalyst.

10. The process of claim 9 wherein the second reaction zone comprises at least one fixed bed reactor.

11. The process of claim 1 wherein the feed is fractionated prior to contacting with the catalyst in the first reaction zone to remove at least a portion of the dienes and alkynes possessing four or more carbon atoms and the resultant feed contains at least 10,000 ppm alkynes and dienes.

12. The process of claim 11 wherein the first reaction zone comprises a fixed bed reactor.

13. The process of claim 12 wherein the fixed bed reactor comprises at least two catalyst beds with intercooling means between the catalyst beds.

14. The process of claim 1 wherein the contacting of the hydrocarbon feed with catalyst is performed under vapor phase conditions.

15. The process of claim 1 wherein the contacting of the hydrocarbon feed with the catalyst is performed under mixed vapor and liquid phase conditions.

16. The process of claim 1 wherein the contacting of the hydrocarbon feed with the catalyst is performed under liquid phase conditions.

17. A process for the selective hydrogenation of one or more alkyne and/or one or more diene in a cracking effluent containing olefin and hydrogen, the process comprising:
feeding the effluent into a catalytic distillation reaction zone under selective hydrogenation reaction conditions in the presence of a selective hydrogenation catalyst wherein both gas and liquid phases are present and wherein the effluent is in the vapor phase containing at least about 10,000 ppm of alkyne(s) and/or diene(s), said selective hydrogenation catalyst including palladium and at least one Group IB metal incorporated into an inorganic support, wherein the surface area of the support is from about 2 to about 20 $m^2/g$, the pore volume is greater than about 0.4 cc/g, at least about 90% of the pore volume is contained in pores with pore diameters larger than about 500 Å and the pore volume of the pores with a pore diameter from about 500 A to about 1,000 Å comprise from about 1 to about 2% of the total pore volume.

18. The process of claim 17 wherein the selective hydrogenation catalyst includes from about 0.01 to about 0.1 weight percent palladium and from about 0.005 to about 0.6 weight percent Group IB metal, the weight ratio of the Group IB metal to the palladium ranging from about 0.5:1 to about 6:1.

19. The process of claim 18 wherein the Group IB metal is silver.

20. The process of claim 17 wherein the catalytic distillation reaction zone comprises a catalytic distillation unit operated as a debutanizer.

21. The process of claim 20 wherein the catalytic distillation unit is operated at a pressure of from about 100 psig to about 400 psig and a catalyst bed temperature of from about 30° C. to about 130° C.

22. The process of claim 17 wherein the catalytic distillation reaction zone comprises a catalytic distillation column operated as a depentanizer.

23. The process of claim 22 wherein the catalytic distillation column is operated at a pressure of from between about 75 psig and 350 psig and a catalyst bed temperature of from about 50° C. to about 150° C.

24. The process of claim 17 wherein the catalytic distillation reaction zone includes at least one fixed bed containing said selective hydrogenation catalyst.

25. The process of claim 17 wherein the catalytic distillation reaction zone includes at least two fixed beds with intercooling means between the beds.

26. The process of claim 17 wherein the alkynes comprise one or more of acetylene, methyl acetylene, ethyl acetylene and vinyl acetylene and the dienes comprise one or more of propadiene, butadiene and isoprene.

* * * * *